United States Patent
Koop et al.

(10) Patent No.: US 6,395,779 B1
(45) Date of Patent: *May 28, 2002

(54) METHOD OF TREATMENT USING PEROXIDIZED LIPIDS

(75) Inventors: Eileen P. Koop, Elizabeth, CO (US); Mary Jo Schwarz, Scottsdale, AZ (US); Stephan Desjonqueres, Maisons Lafitte (FR)

(73) Assignees: Neoteric Cosmetics, Inc., Denver, CO (US); Laboratoires Carilene S.A., Montesson (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/493,392

(22) Filed: Jan. 28, 2000

Related U.S. Application Data

(60) Provisional application No. 60/117,779, filed on Jan. 29, 1999.

(51) Int. Cl.[7] .......................... A61K 31/23; A61K 7/00; A01N 37/02
(52) U.S. Cl. .................. 514/552; 424/401; 514/866
(58) Field of Search .......................... 424/401; 514/552, 514/866

(56) References Cited

U.S. PATENT DOCUMENTS

| | | | |
|---|---|---|---|
| 5,254,585 A | | 10/1993 | Desjonqueres .............. 514/552 |
| 5,985,292 A | * | 11/1999 | Fourneron et al. .......... 424/401 |
| 6,001,378 A | | 12/1999 | Desjonqueres .............. 424/401 |

FOREIGN PATENT DOCUMENTS

| | | | |
|---|---|---|---|
| EP | 391 780 | * | 10/1990 |
| EP | 465 313 | * | 1/1992 |
| EP | 816 478 | * | 1/1998 |
| FR | 2 705 568 | * | 12/1994 |
| FR | 2 750 331 | * | 1/1998 |
| FR | 2 753 374 | * | 3/1998 |

OTHER PUBLICATIONS

Idson, Bernard Ph.D., "Wound Healing", Cosmetic Research Trends, vol. 2, Issue 1, Summer 1994.
"Diabetes Day–by–Day: Skin Care and Common Skin Problems", published by American Diabetes Association, 1997.
Kemp, Randolph, "Microcirculation & DM", published by Mayo Foundation for Medical Education and Research, 1997.

* cited by examiner

Primary Examiner—Jose' G. Dees
Assistant Examiner—Marina Lamm
(74) Attorney, Agent, or Firm—Wolf, Greenfield & Sacks, P.C.

(57) ABSTRACT

A method of therapeutically treating wounds, circulatory insufficiencies and skin disorders, in diabetics, is provided. The method involves the therapeutic application of peroxidized lipids or compositions containing peroxidized lipids to an area of skin of a subject with a diabetic condition including a wound, a skin disorder, or with insufficient circulation. The method is effective for promoting the healing of wounds, in particular, in patients having circulatory insufficiencies and/or diabetes.

9 Claims, No Drawings

METHOD OF TREATMENT USING PEROXIDIZED LIPIDS

This application claims the benefit of U.S. Provisional Application No. 60/117,779 filed Jan. 29, 1999.

BACKGROUND

1. Field of the Invention

The present invention is related generally to the therapeutic application of a peroxidized lipid or a composition containing a peroxidized lipid to promote wound healing and to treat circulatory insufficiencies and skin disorders, particularly in diabetics.

2. Related Art

It is known that many people suffer from circulatory insufficiency of arterial or venous origin, which is often chronic. Circulatory insufficiencies may be local and benign, manifested by, for example, a feeling of painful numbness at the finger ends caused by cold (tingling), or heaviness in the lower limbs. Circulatory insufficiencies may be manifested in much more serious forms associated with an arrest of the blood circulation (ischemia), which is capable of causing localized necrosis. Arterial or venous leg ulcers, for example, are the result of such a circulatory insufficiency and are a clinical manifestation of insufficient irrigation of the superficial and deep tissues by blood flow. Certain peroxidized lipids are known to have a high level of efficacy in tissue revascularization when applied topically. One use of such peroxidized lipids is known to promote increased blood flow in subjects patients suffering from male sexual asthenia, as disclosed in U.S. Pat. No. 5,254,585, issued on Oct. 19, 1993, which is hereby incorporated by reference in its entirety.

Chronic circulatory insufficiency is common in diabetic patients, who are particularly susceptible to problems and disorders associated with poor blood flow, particularly in the extremities. Diabetes affects nearly every part of the body, causing capillary blood vessels to narrow and harden. It has been estimated that up to about one third of diabetics will experience a skin disorder caused or aggravated by the disease. A skin disorder is often the first sign that a person has diabetes. Some skin disorders are common to many people but occur more often and more easily with diabetics. Chronic dry skin, bacterial infections, fungal infections, and itching, occur with many people, especially diabetics. Diabetic dermopathy, necrobiosis, lipodica diabeticorum, diabetic blisters, and eruptive xanthomatosis occur only among diabetics. Many treatments have been proposed for overcoming these insufficiencies. Thus, it has already been recommended to use numerous vasodilative or vasoprotective products by oral or percutaneous administration, often by perfusion. However, these products have many undesirable side-effects, so their use is restricted to the most serious cases of circulatory insufficiency.

Patients with chronic circulatory insufficiency, including diabetics, are particularly susceptible to problems with the wound healing process. The wound healing process involves a complex cascade of biochemical and cellular events to restore tissue integrity following an injury. The wound healing process is typically characterized by four stages: 1) hemostasis; 2) inflammation; 3) proliferation; and 4) remodeling. The synthesis of collagen, which accounts for about 90% of the proteins found in the human dermis, is known to play a role in the necessary biological cascade of wound healing. Collagen has diverse biological roles including morphogenesis (shaping and contouring), tissue repair, remodeling, cellular adhesion, cellular migration, chemotaxis and platelet aggregation. An important factor in the rate of production of collagen is adequate blood flow. Reduced blood flow is a primary causative factor in elongated wound healing time and is also related to the general health aspects of skin.

SUMMARY

In one embodiment, the present invention is directed to a method for treating a wound in a subject with a diabetic condition. The method involves administering a peroxidized lipid to a subject in need of such treatment in an amount effective to promote wound healing in the subject.

In another embodiment, the method is directed to treating a wound in a subject with a diabetic condition otherwise free of symptoms of male sexual asthenia. The method involves administering a peroxidized lipid to a subject in need of such treatment in an amount effective to promote wound healing in the subject.

In another embodiment, the method involves treating a subject with a diabetic condition who has sustained a wound. The method involves administering a peroxidized lipid to a subject in need of such treatment in an amount effective to promote wound healing in the subject.

In another embodiment, the method involves treating a subject with a diabetic condition who has sustained a wound. The subject is otherwise free of symptoms of male sexual asthenia. The method involves administering a peroxidized lipid to a subject in need of such treatment in an amount effective to promote wound healing in the subject.

In another embodiment, the method involves treating a circulatory insufficiency in a subject with a diabetic condition, by administering a peroxidized lipid to a subject in need of such treatment in an amount effective to promote circulation in the subject.

In another embodiment, the method is directed to treating a diabetic skin disorder in a subject. The method involves administering a peroxidized lipid to a subject in need of such treatment in an amount effective to promote healing of the diabetic skin disorder.

According to each of the above-described embodiments, the peroxidized lipid includes at least one peroxide.

DEFINITIONS

"Subject," as used herein, shall mean a human or vertebrate animal including, but not limited to, a dog, cat, horse, cow, pig, sheep, goat, chicken, primate, e.g., monkey, rat, and mouse.

"Diabetic subject: as used herein, shall mean a human or vertebrate animal including, but not limited to, a dog, cat, horse, cow, pig, sheep, goat, chicken, primate, e.g., monkey, rat, and mouse with a diabetic condition.

"Skin disorder," as used herein, means a disturbance of function, structure, or both, resulting from exogenous factors such as poison, trauma or disease.

"Diabetic skin disorder," as used herein, means a skin disorders that may occur in any population, but occurs more frequently in subjects having circulatory insufficiencies and/or diabetes.

"Wound," as used herein, means a trauma to any of the tissues of the body, especially that caused by physical means and with interruption of continuity.

"Peroxidized lipid," as used herein, means any peroxidized lipid compound useful in the present invention including all natural and/or synthetic analogues of peroxidized lipids or lipid-like compounds which possess the biological activity of peroxidized lipids in the skin, such as the promotion of collagen synthesis in the dermis, and increased blood flow, among other effects. Also encompassed within the term "peroxidized lipid" are geometric and stereoisomers of the peroxidized lipids. Biologically active "peroxidized lipids" useful in the methods of the invention include at least one peroxide obtained by the peroxidation of lipids of vegetable origin.

"Composition including peroxidized lipids," as used herein, means a composition including substantial amounts of the previously defined peroxidized lipids. Other materials, or other lipids that do not have the biological activity of the previously described peroxidized lipids may be included in the composition.

"Substantial amount," as used herein, means at least about 2%.

"Emollient," as used herein, refers to the non-irritating character of the composition as a whole. That is, the nature of the vehicle and amount of peroxidized lipid therein should be selected so as to provide a sub-irritating dose for topical application.

An "effective amount" as used herein, is a dosage of the peroxidized lipid sufficient to provide a medically desirable result.

"Carrier," as used herein, denotes an organic or inorganic ingredient, natural or synthetic, with which the active ingredient is combined to facilitate the application.

"Pharmaceutically-acceptable carrier," as used herein, means one or more compatible solid or liquid filler, diluents or encapsulating substances which are suitable for administration onto a human or other animal.

"Long-term sustained release," as used herein, means an implant constructed and arranged to deliver therapeutic levels of an active ingredient for at least 30 days, and preferably 60 days.

DETAILED DESCRIPTION

The present invention is directed to methods of applying a peroxidized lipid or a composition that includes peroxidized lipids. The method involves the therapeutic application of peroxidized lipids, or compositions containing peroxidized lipids, to treat skin disorders, circulatory insufficiencies, wounds to the dermis, and wounds to the epidermis, by applying the peroxidized lipid or a composition containing the peroxidized lipid, to an area of skin on a subject that includes such a condition. The present invention is based on the surprising discovery that certain peroxidized lipids may modify the wound healing process, and contribute to, inter alia, therapeutically treating subjects having various conditions or disorders including, but not limited to, circulatory insufficiencies, skin disorders, wounds to the skin dermis or epidermis. Although not wishing to be bound by any theory, it is thought that the methods described herein are effective due to the release of free oxygen and/or the promotion of collagen production.

Advantages of treatment with the peroxidized lipids according to the methods of the invention may include, inter alia, increased collagen production, faster wound healing, particularly in diabetics, increased blood flow, and normalizing of the epidermis resulting in smoother, less dry, and less rough skin. Because of this activity, they may promote and accelerate the healing of wounds in compromised tissue. Further, the production of new collagen may repair damaged skin. Still further, treatment with peroxidized lipids according to the present invention may raise the surface temperature of the skin due to greater flow of blood, increasing acuity to pain and irritation, and allowing the skin to become more reactive to chemical insults. Such increased sensitivity of the skin treated with peroxidized lipids may provide an early warning system to older people and diabetics to minimize damage before pain or irritation is felt.

In one aspect, the methods of the invention are useful for treating a wound to the dermis or epidermis. The present method is particularly useful in treating subjects with circulatory insufficiencies or diabetes. Injury to the skin may lead to a number of undesirable health conditions, including, for example, problems with the wound healing process. When problems with the wound healing process become very severe, then management of the wound typically becomes invasive. In some instances of severe circulatory insufficiencies or complications related to diabetes, amputation may be required. Many treatments have been proposed for overcoming such insufficiencies, as well as for alleviating other disorders associated with chronic circulatory insufficiency. One attempt to modify the wound healing process involved the topical application of B-Glucans, a macrophage stimulator, resulting in more rapid epithelization, earlier angiogenesis, increased collagen formation, and increased breaking strength of wounds. Various vitamins and minerals are known to modulate the connective tissue formation phase of wound healing. Others have attempted to modify the wound healing process by stimulating the production or biosynthesis of collagen. One attempt at collagen stimulation includes using vasodilator prostaglandins $PGE_1$ and $PGI_2$, which have shown clinical promise in patients with impaired blood supply from vascular diseases. Stimulation of collagen and glycosaminoglycan deposition, accelerated epidermal regeneration, and stimulation of angiogenesis has been shown in a number of animal wound models by the topical application of epidermal growth factor (EGF). Other agents under study include platelet-derived growth factor (PDGF), fibroblast growth factor (FGF), and transforming growth factors-alpha and beta ($TGF\%_{,B}$).

The conditions and/or disorders described above are not associated with male sexual asthenia, which is a particular category of circulatory insufficiency. Diabetes, in particular, is unrelated to male sexual asthenia. Thus, the preferred group of patients treatable by the methods of the present invention are subjects free of symptoms of circulatory insufficiencies, as well as subjects that are free of male sexual asthenia. The preferred subjects are also otherwise free of any other condition calling for peroxidized lipid treatment, such as being free of symptoms calling for vasodilative or vasoprotective products.

The method according to any of the embodiments of the invention described above involves the application of a composition containing substantial amounts of peroxidized lipids. Preferably, the peroxidized lipids used in the methods of the invention include at least one peroxide obtained by the peroxidation of lipids of vegetable origin, for example, in the form of at least one natural vegetable oil. Such oils are preferably selected from sweet-almond oil, hazelnut oil, peanut oil, maize oil, grapeseed oil, sesame oil and safflower oil. The peroxidized lipids described above may be derived from commercially available compounds using routine chemical procedures known to those of ordinary skill in the art. The peroxidized lipids useful in the methods of the invention are known products prepared from lipids, for example, by saturation with oxygen and intense and controlled exposure to ultraviolet rays, as described in documents: BSM No. 2330 M; EP-A-293 535; FR-A-C-2591 112; EP-A-225 832; EP-A-225 833; EP-A-226 506; FR-A-1 461 744; FR-A-2 539 142; and EP-A-117 961.

The peroxidized lipids used in the methods of the invention may vary in chemical nature, but must necessarily have a degree of peroxidization of between 50 and 200 milliequivalents per kilogram, and more preferably of between 50 and 150 milliequivalents per kilogram measured by the AFNOR method. In one particular embodiment, such peroxidized lipids have a content of oxidized glycerides of between 5 and 40%. A preferred method involves the topical application of a pharmaceutical composition including from about 2 to about 99% peroxidized lipids. Although not required, it is preferred that the pharmaceutical composition includes about 1% of fragrance, as well as pharmaceutically acceptable excipients and demineralized water.

One preferred peroxidized lipid has the general formula:

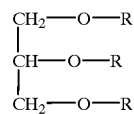

where R is an octadecenoic or peroxidized octadecenoic acid, as disclosed in the above-referenced U.S. Pat. No. 5,254,585, which is incorporated herein by reference in its entirety. The composition may also include, for example, lipids with different functional groups, including, but not limited to, septadecenoic or peroxidized septadecenoic acid, or nonadecenoic or peroxidized nonadecenoic acid functional groups.

The peroxidized lipids described above are administered in effective amounts. The effective amount will vary with the particular condition being treated, the age and physical condition of the subject being treated, the severity of the condition, the duration of the treatment, the nature of the concurrent therapy (if any), the specific route of administration, and like factors within the knowledge and expertise of the health practitioner. For example, an effective amount for treating circulatory insufficiency would be an amount sufficient to promote increased blood flow (see examples). Also as an example, an effective amount for treating wounds would be an amount sufficient to halt the development or further progression of necrosis. Thus, it will be understood by those skilled in the art that the peroxidized lipids of the invention may be used to treat circulatory insufficiencies in subjects at risk of developing complications from circulatory insufficiency. It is preferred generally that a maximum dose be used, that is, the highest safe dose according to sound medical judgement.

Generally, doses of the active compound will include between 50 and 200 milliequivalents per kilogram, and preferably of between 50 to 150 milliequivalents per kilogram. It is expected that doses ranging from 50 to 150 milliequivalents per kilogram will be suitable, preferably topically, and one or several administrations per day. In the event that a response on the subject is insufficient at the initial dose is supplied, higher doses (or effectively higher doses by a different, more localized delivery route) may be employed to the extent that patients tolerance permits. Multiple doses per day are contemplated to achieve and maintain a medically desirable result.

When administered, the pharmaceutical preparations of the invention are applied in pharmaceutically-acceptable amounts and in pharmaceutically-acceptable compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may be conveniently used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts may be prepared as alkaline metal or alkaline earth salts, such as sodium, potassium or calcium salts.

The peroxidized lipids may be combined, optionally, with a pharmaceutically-acceptable carrier. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including, for example, acetic acid in a salt; citric acid in a salt; boric acid in a salt; and phosphoric acid in a salt.

The pharmaceutical compositions also may contain, optionally, suitable preservatives to stabilize the composition, and/or prevent the growth of bacteria and/or molds. A variety of suitable materials known in the art of pharmaceutical and cosmetic formulation may be used in this context, for example, methyl paraben, benzalkonium chloride, benzylparaben, calcium acetate, captan, chloroacetamide, dichlorobenzyl alcohol, DMDM hydantoin, imidazolidinyl urea, isopropylparaben, quaternium-15, sodium benzoate, and the like.

Other components may also be included in the overall composition to impart other desirable properties to the formulation, for example, vitamins, fatty acid esters, ultraviolet light absorbers, peripheral vasodilators such as methyl salicylate and nicotinic acid and its esters, herbal additives, powdered milk, proteolytic enzymes, vegetable powders, fruit extracts, egg solids or oil, starches, clays, amino acids, proteins, astringents, drugs, and the like.

One preferred composition has the characteristics shown below in Table 1.

TABLE 1

| COMPOSITION | Wt % |
|---|---|
| Demineralized water q.s.p. | 100 |
| Peroxidized lipids | 25.0 |
| Non-ionic emulsifier | 6.0 |
| Stearic acid | 5.0 |
| propylene glycol | 3.0 |
| Cetyl alcohol | 2.0 |
| Fragrance | 0.8 |
| Silicones | 0.5 |
| Antimicrobial agent | 0.3 |
| Triethanoiamine | 0.2 |

A variety of administration routes are available. The particular mode selected will depend of course, upon the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. According to one particular characteristic of the invention, these products are used for the preparation of a pharmaceutical composition intended for local topical application, and may be in the form of a cream, liquid, solution, gel, soft capsules, or transdermal patches containing the peroxidized lipids.

The pharmaceutical compositions may conveniently be presented in unit dosage form and may be prepared by any of the methods well-known in the art of pharmacy. All methods include the step of bringing the peroxidized lipids into association with a carrier which includes one or more accessory ingredients. In general, the compositions are prepared by uniformly and intimately bringing the peroxidized lipids into association with a liquid carrier, a finely divided solid carrier, or both, and then, if necessary, shaping the product. Other delivery systems may include time-release, delayed release or sustained release delivery systems. Such systems may avoid repeated administrations of the peroxidized lipids described above, increasing convenience to the subject and the physician. Use of a long-term sustained release systems may be particularly suitable for treatment of chronic conditions. Long-term sustained release implants are well-known to those of ordinary skill in the art and include some of the release systems described above.

Thus, one aspect of the invention provides the following benefits: faster wound healing; normalization of the epidermis; and promotion of collagen production. Accordingly, peroxidized lipids promote the formation of a more normal dermis. Because of this activity, they may promote and accelerate the healing of wounds in compromised tissue.

Still further, treatment with peroxidized lipids according to the present invention may raise the surface temperature of the skin due to greater flow of blood, increasing acuity to pain and irritation, and allowing the skin to become more reactive to chemical insults. Such increased sensitivity of the skin treated with peroxidized lipids may provide an early warning system to older people and diabetics so that too much damage is not done before the pain or irritation is felt.

The present invention will be further illustrated by the following examples, which are intended to be illustrative in nature and are not to be considered as limiting the scope of the invention.

EXAMPLE 1

The present example illustrates the preparation of a pharmaceutical composition based on peroxidized lipids originating from a commercially available virgin safflower oil.

Commercially available virgin safflower oil is subjected to peroxidation treatment as disclosed in FR-A-2 461 744. The method includes storing the safflower oil in a stainless steel vat covered with a hinged hood capable of collecting the vapors and acting as a support for an ultraviolet radiation lamp, for example a PHILIPS type HP 4 of 125 W. Air is fed continuously fed to the vat by an air pump, for example, at a rate of 30 1/minute to produce a bubbling effect. The vat is also heated by resistors supplied with electricity so as to maintain a temperature of 80° to 100° C. The oil is kept under these conditions for a period of 20 to 35 hours, depending on the origin of the lipids, especially for 25 hours in the case of the safflower oil considered in this Example, in order to obtain a degree of peroxidation according to the invention. The oil is then stored in a storage tank for receiving peroxidized safflower oil which may come from several peroxidation vats.

The characteristics of the safflower oil before and after peroxidation are shown below in Table 2.

TABLE 2

|  | Before Treatment | After Treatment |
| --- | --- | --- |
| Peroxide number | 18.70 meq/kg | 149.0 meq/kg |
| Oxidized glyceride | 4.18% | 11.30% |
| Viscosity at 50° C. | 23.2 centistokes | 25.9 centistokes |

EXAMPLE 2

The present example is designed to provide measurement of the deep and peripheral circulation by Rheoplethysmography after topically applying the pure peroxidized lipid obtained in Example 1.

The test is performed over an area of 10×10 cm on the calves (5 cm below the lower end of the knee-cap). These zones are covered, by gentle massage, with a few drops of pure peroxidized safflower oil obtained in Example 1. The measurements are made at T=O (before application of the products) and T=5 min after application of the pharmaceutical composition, once on the right calf and once on the left calf. Two electrodes for measuring blood volume variations are placed at the upper and lower ends. A cuff is placed around the thigh, and inflated to a pressure of 5 cm Hg so as to allow blood flow to enter the limb under examination while preventing the "venous return." The volume variations are recorded in this limb segment. At the moment of occlusion, there is an increase up to a maximum value. This initial volume variation represents the increase in arterial flow. When the maximum value is reached, the cuff is deflated. The venous drainage takes place with a curve of initially rapid and then slow decay. The angle corresponding to the ascending gradient of the filling curve was studied. A comparable test was carried out in the absence of the composition.

Comparison of the curves obtained after application of the peroxidized safflower oil according to the invention with the curves in the absence of the composition made it possible to discern a significant increase in the arterial volumes in the first case, represented by an increase in the angle from 0.5 to 1.4 and from 0.4 to 1.5. That is, local application of lipids used according to the invention provide an increase in flood flow of more than 100%.

EXAMPLE 3

The present example is designed to provide comparative Doppler measurements of circulation rates on patients using the pure peroxidized lipid obtained in Example 1.

The study was performed with a subject sitting down with hands placed on a flat surface. The radial, cubital, interosseous and pulpal arteries were studied by the Doppler method in the basal state T=O. The superficial veins were also examined. Pure peroxidized safflower oil according to the invention, obtained in Example 1, was spread over the fingers of both of the subject's hands. As it was impossible to study all ten fingers at once, the following were arbitrarily studied: the flow in the distal phalanges (pulpal flow) of the right index finger and ring finger and the flow in the left thumb (interosseous space). A small amount of product was spread over each of these segments with gentle massage. The subject did not move their hands during the 30 minutes of examination. Blood flow was recorded after 1 min, 5 min, 10 min and 30 min. Measurements were also made up to 6 h.

The results obtained showed a very marked increase in both the arterial and the venous flows (increase in the systolic-diastolic areas) from the 1 st minute, with maintenance beyond the 30th min. The curves also showed this maintenance up to 6 h. No pain was observed in the skin of the fingers covered with the product. No redness was observed, which rules out a revulsive action of the product.

EXAMPLE 4

This experiment was performed to assess the efficacy of a composition including the pure peroxidized lipid obtained in Example 1 to promote wound healing in diabetic subjects.

A composition containing 20% of the pure peroxidized lipid obtained in Example 1 was used in a double blind, placebo controlled experiment designed to assess the efficacy of treatment to enhance the wound healing process in diabetic subjects. Thirty-four subjects with physician diagnosed Type I or II diabetes participated in the experiment. Subjects with known sensitivities (allergies, irritation, etc.) were excluded from participation.

At Visit 2 (baseline), after anesthetization, a laser was used to create a single wound of uniform depth and diameter on the ventral aspect of the right and left forearms of each subject. Each wound was examined to establish a baseline for size (diameter), closure appearance, erythema, and edema.

Subjects were instructed to apply the composition in an amount sufficient to cover the wound. The product was rubbed into the wound slightly but not necessarily until it absorbed into the skin. Each wound was placed in one of three treatment groups:

A: the test group (treatment containing the pure peroxidized lipids active ingredient);

B: the placebo group (product containing no active ingredient); and

C: the control group (no product application).

Each subject was given one or two test materials (depending on the groups in which they were placed), bandages for covering the wounds, detailed oral and written instructions regarding the application of the test material(s), a daily diary, and a cleanser for showering/bathing during the course of the study. A single macro color photograph was taken of approximately five wounds in each test group.

Subjects were graded for approximately two weeks after the wounds were created. Visit 2 took place three days after the wound was made, and Visits 3–7 took place six, eight, ten, twelve, and fourteen days after the wound was made, respectively. Following three, six, eight, ten, twelve, and fourteen days of product use (Visits 2 through 7), the study physician graded each wound for size (diameter), closure appearance, erythema, and edema. Subjects in the photography group also had a single macro color photograph taken of the wound(s) at each of these visits. At Visit 7, subjects completed a post-usage questionnaire.

Table 7 presents the results of the wound examinations for size (diameter in mm), closure appearance, erythema and edema at baseline and following three, six, eight, ten, twelve, and fourteen days of product use. Grading for closure appearance were based on a 0–10 scale in which 0=no closure and 10=complete closure. Grading for erythema and edema were based on a four-point scale in which 0=none, 1=mild, 2=moderate, 4=strong. A "↑" indicates a significant increase ($\sigma=0.05$), compared to baseline, and a "↓" indicates a significant decrease ($\sigma=0.05$), compared to baseline.

TABLE 3

| Grading Parameter | Days of Use | Peroxidized Lipids (N = 24) | Placebo (N = 22) | Control (N = 22) |
| --- | --- | --- | --- | --- |
| Diameter (mm) | Baseline | 6.00 | 6.00 | 6.00 |
|  | Day 3 | 3.83↓ | 3.77↓ | 3.68↓ |
|  | Day 6 | 3.00↓ | 3.00↓ | 2.82↓ |
|  | Day 8 | 2.17↓ | 2.18↓ | 2.05↓ |
|  | Day 10 | 1.13↓ | 1.23↓ | 1.32↓ |
|  | Day 12 | 0.67↓ | 0.82↓ | 0.64↓ |
|  | Day 14 | 0.38↓ | 0.55↓ |  |
| Closure appearance | Baseline | 1.00 | 1.00 | 1.00 |
|  | Day 3 | 4.13↑ | 4.14↑ | 4.27↑ |
|  | Day 6 | 5.08↑ | 5.05↑ | 5.36↑ |
|  | Day 8 | 6.63↑ | 6.59↑ | 6.86↑ |
|  | Day 10 | 8.29↑ | 8.32↑ | 8.09↑ |
|  | Day 12 | 9.08↑ | 8.95↑ | 9.14↑ |
|  | Day 14 | 9.58↑ | 9.41↑ | 9.82↑ |
| Erythema | Baseline | 0.00 | 0.00 | 0.00 |
|  | Day 3 | 1.29↑ | 1.36↑ | 0.50↑ |
|  | Day 6 | 1.50↑ | 1.73↑ | 1.00↑ |
|  | Day 8 | 1.42↑ | 1.41↑ | 0.91↑ |
|  | Day 10 | 1.25↑ | 1.41↑ | 0.82↑ |
|  | Day 12 | 0.92↑ | 1.14↑ | 0.55↑ |
|  | Day 14 | 0.88↑ | 1.00↑ | 0.55↑ |
| Edema | Baseline | 0.00 | 0.00 | 0.00 |
|  | Day 3 | 0.25↑ | 0.45↑ | 0.00 |
|  | Day 6 | 0.25↑ | 0.59↑ | 0.05 |
|  | Day 8 | 0.08 | 0.23↑ | 0.00 |
|  | Day 10 | 0.08 | 0.14 | 0.00 |
|  | Day 12 | 0.00 | 0.00 | 0.00 |
|  | Day 14 | 0.00 | 0.00 | 0.00 |

Results of the study showed that global assessment of wound healing was improved with the 20% peroxidized lipid composition 77.3% of the time versus the placebo composition. Trends in the data also favor the pure peroxidized lipids as being the more efficacious product for both objective and subjective scoring.

All treatment groups showed significant improvements in wound diameter and closure appearance at each study visit starting with the first day of grading (day 3). Grades for erythema and edema started as zero ("0") for all subjects immediately after the wound was created. At the first two study visits (days 3 and 6 of grading), scores increased slightly as a mild inflammatory response developed. At the last four study visits (days 8–14 of grading), scores showed a steady decline toward a score of zero ("0").

A statistical analysis between the three groups of data showed a few significant differences during the course of the study. In most cases, the untreated control group showed a more rapid healing process than treatment groups using the peroxidized lipids or placebo. The diameter of the wound closure is believed to be smaller due to the dryness of the wound and the subsequent tightening and drawing in of the edges. The slightly higher scores for erythema, edema, and wound closure may be due to a mild irritant response caused by application of the products to the exposed living cellular tissue. Alternatively, the control group could have appeared to heal faster due to a masking of the underlying healing process (epithelialization) by the formation of a hard, dried exudate ("scab") over the wound.

Among the two treated sites, the data show that the peroxidized lipids outperformed the placebo for all of the grading parameters at most of the six study visits. For wound diameter, the peroxidized lipids performed better than the placebo for the last four study visits (days 8, 10, 12 and 14). The peroxidized lipids performed better than the placebo on days 6, 8, 12 and 14 for closure appearance, and on days 3, 6, 10, 12 and 14 for erythema. The peroxidized lipids also outperformed the placebo for edema on all days that the two groups showed non-zero scores (days 3, 6, 8 and 10). Overall, the peroxidized lipids showed a better performance than the placebo in seventeen of twenty-two cases (77.3% of the time). This count does not include two days when both groups produced scores of zero ("0") for edema.

EXAMPLE 5

An open clinical study of 20 Type I or II diabetics showing signs of clinical and/or dermatological disorders of the lower legs and feet was conducted using a composition containing 30% of pure peroxidized lipid as obtained in Example 1.

Clinical symptoms included diabetic neuropathy, edema, hyperkeratosis, cracks, ulcerations, inflammation, mycosis and cutaneous dryness. The disorders studied may be linked to a diabetic neuropathy (hot or cold feet, edema, perforating neurotrophic ulcer, heavy legs) or to a distal diabetic arthritis (cold feet, cutaneous necrosis, previous toe amputation). It may also be a matter of plantar abnormalities not specifically related to diabetes (hyperkeratosis, plantar racks, inflammation, and corns) concerning rather obese diabetics, the consequences of venous insufficiency (heavy legs, ulcerations edema), interdigital or ungual mycotic infections and, lastly, cutaneous dryness.

Only the initial serious symptoms (++) and very serious (+++) were retained for the

| Hot feet: | 5 cases/20 patients (25%) |
| --- | --- |
| Cold feet: | 9 cases (45%) |
| Edema: | 8 cases (40%) |
| Hyperkeratosis: | 8 cases (40%) |
| Plantar cracks: | 5 cases (25%) |
| Ulcerations: | 2 cases (10%) |
| Perforating ulcer: | 1 case (5%) |
| Inflammation and/or corns: | 5 cases (25%) |
| Interdigital mycosis: | 1 case (5%) |
| Ungual mycosis: | 6 cases (30%) |
| Cutaneous dryness: | 10 cases (50%) |
| Heavy legs: | 15 cases (75%) |

Subjects were given samples of cream that they were instructed to apply morning and evening for a period of one month on the feet and the lower third of each leg. Subjects were seen again 15 days after inclusion (visit D15), and again 15 days later at the end of the therapeutic trial (visit D30). Subjects were instructed to apply the composition twice daily to their feet and lower limbs. Clinical, physician evaluations were conducted at 15 and 30 days. Significant regression of clinical and/or dermatological symptoms were observed for all parameters except ulcerations and mycosis.

A favorable or very favorable result from treatment was obtained in 14 cases (70%). The dominant pathologies that clearly improved are given by decreasing order of frequency:

| Neuro-sensory disorders | (7 cases) |
| --- | --- |
| Edema | (4 cases) |
| Heavy legs | (4 cases) |
| Plantar cracks | (3 cases) |
| Hyperkeratosis | (3 cases) |
| Cutaneous dryness | (2 cases) |
| Venous insufficiency in lower limbs | (2 cases) |
| Inflammation and corns | (1 case) |

A very weak or null effect was reported in 5 patients (25%). The dominant pathologies that did not improve or only weakly improved are given by decreasing order of frequency:

| Hyperkeratosis | (2 cases) |
| --- | --- |
| Inflammation and corns | (2 cases) |
| Cutaneous dryness | (1 case) |

Significant regressions of clinical and/or dermatological symptoms were obtained for the following situations:

| Hot feet: | 3 times/5 (60%) |
| --- | --- |
| Cold feet: | 6 times/9 (67%) |
| Edema: | 5 times/8 (62.5%) |
| Hyperkeratosis: | 2 times/8 (25%) |
| Plantar cracks: | 4 times/5 (80%) |
| Ulcerations: | 0 times/2 (0%) |
| Perforating ulcer: | 0 times/1 (0%) |
| Inflammation, corns: | 3 times/5 (60%) |
| Interdigital mycosis: | 0 times/5 (0%) |
| Ungual mycosis: | 0 times/1 (0%) |
| Cutaneous dryness: | 8 times/10 (80%) |
| Feelings of heavy legs: | 10 times/15 (67%) |

The most significant results were therefore observed on cutaneous dryness, scarification of plantar cracks (non-specific dermatological symptoms), feelings of heavy legs, feelings of hot and/or cold feet, and edema (functional and/or clinical abnormalities most often related to the development of a diabetic neuropathy).

Several patients suffering from paresthesia and pains caused by documented diabetic neuropathy (positive electromyogram, positive clinical observation) showed significant improvement of symptoms under treatment:

Disappearance of nocturnal cutaneous burning sensations (patient #1)

Disappearance of sensory disorders (patient #4)

Disappearance of paresthesia in extremities (patient #5)

Idem (patient #14)

Very clear improvement of sensations of hot and cold feet (patient #15)

The best results in statistical terms were observed above all for neuro-sensory disorders in patients suffering from diabetic neuropathy and among patients with heavy legs or who complained of plantar cracks often associated with hyperkeratosis phenomena.

Although particular embodiments of the invention have been described in detail for purposes of illustration, various changes and modifications may be made without departing from the scope and spirit of the invention. Accordingly, the invention is not to be limited except as by the appended claims.

What is claimed is:

1. A method for treating a wound in a subject having a diabetic condition, comprising:

administering a preparation including only one active ingredient for healing, to a diabetic subject in need of treatment in an amount effective to promote wound healing in the subject, wherein the one active ingredient for healing is a peroxidized lipid, and wherein the peroxidized lipid includes at least one peroxide.

2. The method of claim 1, wherein the peroxidized lipid has the following formula:

$$\begin{array}{l} CH_2\text{---}O\text{---}R \\ | \\ CH\text{---}O\text{---}R \\ | \\ CH_2\text{---}O\text{---}R \end{array}$$

wherein R=octadecenoic or peroxidized octadecenoic acids.

3. The method of claim 2, wherein the subject has a skin disorder.

4. The method of claim 2, wherein the subject has a circulatory insufficiency.

5. A method for treating a diabetic subject who has sustained a wound, comprising:

administering a preparation including only one active ingredient for healing, to a diabetic subject in need of such treatment in an amount effective to promote wound healing in the subject, wherein the one active ingredient for healing is a peroxidized lipid, and wherein the peroxidized lipid includes at least one peroxide.

6. The method of claim 5, wherein the peroxidized lipid has the following formula:

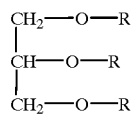

wherein R=octadecenoic or peroxidized octadecenoic acids.

7. The method of claim 6, wherein the subject has a skin disorder.

8. A method of treating a diabetic skin disorder in a subject, comprising:

administering a preparation including only one active ingredient for healing, to a subject in need of such treatment in an amount effective to promote healing of the diabetic skin disorder in the subject, wherein the one active ingredient for healing is a peroxidized lipid, and wherein the peroxidized lipid includes at least one peroxide.

9. The method of claim 8, wherein the peroxidized lipid has the following formula:

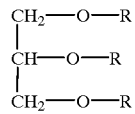

wherein R=octadecenoic or peroxidized octadecenoic acids.

* * * * *